United States Patent [19]

Bernheim et al.

[11] Patent Number: 4,735,685
[45] Date of Patent: Apr. 5, 1988

[54] PROCESS FOR SIZING PAPER OR CARDBOARD WITH ANIONIC HYDROPHOBIC SIZING AGENTS AND CATIONIC RETENTION AIDS

[75] Inventors: Michael Bernheim, Aystetten, Fed. Rep. of Germany; Hubert Meindl, Riehen; Peter Rohringer, Schönenbuch, both of Switzerland

[73] Assignee: Ciba-Geigy Corporation, Ardsley, N.Y.

[21] Appl. No.: 773,705

[22] Filed: Sep. 9, 1985

[30] Foreign Application Priority Data

Sep. 13, 1984 [CH] Switzerland ............ 4390/84

[51] Int. Cl.$^4$ ............... D21H 3/08
[52] U.S. Cl. ............... 162/135; 162/158; 162/164.3; 162/164.6; 162/166; 162/167; 162/168.2; 162/175; 162/178; 162/179; 162/181.1; 427/391; 427/395
[58] Field of Search ............ 162/158, 179, 168.2, 162/135, 164.6, 175, 164.3, 166, 167, 178; 106/243, 287.25; 427/395, 391

[56] References Cited

U.S. PATENT DOCUMENTS

| | | | |
|---|---|---|---|
| 3,194,728 | 7/1965 | Stump | 162/179 |
| 3,403,113 | 9/1968 | Diethehm et al. | |
| 3,491,064 | 1/1970 | Enders et al. | |
| 3,509,098 | 4/1970 | Curchod et al. | |
| 3,652,563 | 3/1972 | Petersen et al. | 162/158 |
| 3,700,623 | 10/1972 | Kolm | |
| 3,821,075 | 6/1974 | Bills | 162/179 |
| 3,931,063 | 1/1976 | Renner | |
| 4,034,040 | 7/1977 | Cronin et al. | |
| 4,058,537 | 11/1977 | Mueller | |
| 4,065,349 | 12/1977 | Bateman et al. | |
| 4,279,794 | 7/1981 | Dumas | |
| 4,402,708 | 9/1983 | Oswald | |

FOREIGN PATENT DOCUMENTS

| | | |
|---|---|---|
| 96654 | 12/1983 | European Pat. Off. ............ 162/179 |
| 2459165 | 6/1976 | Fed. Rep. of Germany . |
| 865727 | 4/1961 | United Kingdom . |
| 1043437 | 9/1966 | United Kingdom . |
| 1125486 | 8/1968 | United Kingdom . |
| 1318244 | 5/1973 | United Kingdom . |
| 1533434 | 11/1978 | United Kingdom . |

OTHER PUBLICATIONS

Casey, *Pulp and Paper*, vol. III, (1981), pp. 1574, 1577, 1602, 1603, 1604, 1914, 1915.
CTFA Cosmetic Ingredient Dictionary, 3rd ed. (1982).
Tappi, vol. 57, No. 1, Jan. 1974, pp. 97–100.
Tappi, vol. 64, No. 6, Jun. 1981, pp. 57–61.
Chem. Abstr. 90:86958m, 25-Noncondensed Aromatics, vol. 90, 1979, p. 577.

*Primary Examiner*—Peter Chin
*Attorney, Agent, or Firm*—Edward McC. Roberts

[57] ABSTRACT

Anionic sizing agents containing anhydride groups, which are novel compounds and which contain a single N,N-$C_6$-$C_{22}$di(alkyl- or alkenyl)amido group, a N-$C_6$-$C_{22}$(alkyl- or alkenyl)amido group or a $C_6$-$C_{22}$-(alkyl or alkenyl) ester group as hydrophobic substituent, and at least one anionic group in acid or salt form, in particular the anhydride of a N,N-$C_6$-$C_{22}$dialkylamido- or N,N-$C_6$-$C_{22}$dialkenylamidocarboxylic acid, the anhydride of a N-$C_6$-$C_{22}$alkylamido- or N,N-$C_6$-$C_{22}$alkenylamidocarboxylic acid, or the $C_6$-$C_{22}$alkyl ester or $C_6$-$C_{22}$alkenyl ester of an aromatic tetracarboxylic acid anhydride or a salt thereof, are particularly suitable, together with commerically available retention aids, for use in a process for pulp-sizing or surface-sizing paper or cardboard.

15 Claims, No Drawings

PROCESS FOR SIZING PAPER OR CARDBOARD WITH ANIONIC HYDROPHOBIC SIZING AGENTS AND CATIONIC RETENTION AIDS

The present invention relates to a process for sizing paper, which comprises using, in addition to commercially available retention aids, an aromatic sizing agent containing anhydride groups and at least one anionic or acid group.

A process for sizing paper using an aromatic sizing agent that contains anhydride groups, together with commercially available retention aids, is disclosed in e.g. U.S. Pat. No. 4,065,349. However, unlike the sizing agent of this invention, which must carry an anionic or acid group, the sizing agent employed in this known process preferably does not contain such a group. The sizing agent employed in the known process is in particular the monoester of an aromatic tricarboxylic acid anhydride, e.g. the 4-n-octadecyl ester of trimellitic anhydride, which does not contain an acid group, whereas in the process of the present invention the monoester of an aromatic tetracarboxylic acid anhydride, e.g. the 4-n-octadecyl monoester of pyromellitic anhydride which contains an acid carboxyl group, is used as sizing agent.

It has now been found that it is possible to obtain substantially better sizing effects (determined e.g. by the water absorption according to Cobb or by the ink flotation time) by using aromatic sizing agents which, in addition to anhydride groups, contain e.g. an acid carboxyl group, together with commercially available retention aids, than by using the sizing agents of U.S. Pat. No. 4,065,349, which contain anhydride groups but no acid group, in particular no carboxyl group, together with commercially available retention aids.

The present invention has for its object to provide the paper manufacturer with readily available sizing agents which can be obtained in simple manner and which, when combined in novel manner with conventional cationic retention aids, are able to effect good sizing in the manufacture of paper from fibre suspensions (pulp or internal sizing) as well as in the manufacture of paper with sized surface (surface-sizing).

Accordingly, the present invention relates to a process for sizing paper or cardboard, i.e. to a process for the manufacture of pulp-sized paper or cardboard or of surface-sized paper, which comprises using at least (A) one novel aromatic sizing agent which contains an anhydride group, a single N,N-dialkylamido or N,N-dialkenylamido group, N-alkylamido or N-alkenylamido group or alkyl or alkenyl ester group containing at least 6 carbon carbons in the alkyl or alkenyl moiety, and at least one anionic group in salt form or in acid, i.e. free, form, and (B) one polymeric cationic retention aid.

In the process of this invention for the pulp-sizing of paper or cardboard, components (A) and (B) are added, in any order or simultaneously, to aqueous cellulose-containing pulp suspensions that may also contain fillers, whereas in surface-sizing the paper is impregnated with an aqueous sizing liquor which contains components (A) and (B), and dried.

Further objects of the invention are:

The aqueous compositions for carrying out the paper sizing process, which compositions contain, if the sizing agent (A) and the retention aid (B) are added separately, in any order, to the fibre suspension for pulp-sizing, only the sizing agent (A) which is at least partly in salt form, together with optional conventional auxiliaries, or, if the sizing agent (A) and the retention aid (B) are added simultaneously to the fibre suspension for pulp-sizing, or are used as sizing liquor for surface-sizing paper, contain the sizing agent (A) which may be at least partially in salt form as well as the retention aid (B), together with optional conventional auxiliaries, the paper or cardboard sized by the process of the present invention, the use of the sizing agent (A) of the indicated kind for sizing paper or cardboard, and the novel compounds employed as sizing agent (A) and the process for the preparation thereof by methods which are known per se.

As mentioned at the outset, the salient feature of the sizing agents (A) of this invention is that they generally contain at least one anionic group which is usually in the form of an acid carboxyl, hydroxyl or sulfo group, with sulfo and, in particular, carboxyl groups being preferred. Sizing agents which contain two such anionic groups or, preferably, only one such group, are preferred. If such groups are in salt form, e.g. as amine, ammonium or sodium salts, they are able to form anions in aqueous medium at the pH values usually prevailing in fibre suspensions during paper manufacture. Under the indicated conditions, the cationic retention aids (B) are for their part also able to form cations. The ability of the sizing agents to form anions and of the retention aids to form cations can also be termed anionic and cationic respectively. Thus, the sizing agents and the retention aids can also be termed anion-liberating sizing agents and cation-liberating retention aids.

The sizing agents (A) are also characterized by the feature that they contain a single N,N-dialkylamido or N,N-dialkenylamido group, N-alkylamido or N-alkenylamido group or alkyl or alkenyl ester group as hydrophobic substituent. Each of the alkyl or alkenyl moieties of the indicated amide or ester groups, independently of the other, contain at least 6, in particular 6 to 22, preferably 11 to 22 and, most preferably, 16 to 20 carbon atoms. Alkyl groups are preferred to alkenyl groups and are derived in general from unsaturated or, preferably, saturated secondary or primary fatty amines or, preferably, fatty alcohols. Symmetrical secondary amines in which the two alkenyl or alkyl moieties are identical are preferred to the asymmetrical secondary amines in which the two alkyl or alkenyl moieties are different. The fatty amines and fatty alcohols are in turn derived from unsaturated or, preferably, saturated fatty acids of 6 to 22, preferably 11 to 22 and, most preferably, 16 to 20 carbon atoms. Such acids are for example capronic acid, preferably caprylic acid, capric acid, lauric acid, myristic or myristoleic acid, palmitoleic acid, eleostearic acid, clupadonic acid, in particular oleic acid, elaidic acid, erucic acid, linolic acid and linoleic acid. Palmitic, stearic, oleic and behenic acid are particularly important, with palmitic and stearic acid being preferred. Also suitable are readily accessible technical, mixtures of these fatty acids. Synthetic fatty acids and fatty alcohols which are prepared e.g. by oxosynthesis also fall within the above definition.

Representative examples of preferred symmetrical secondary amines from which the N,N-dialkylamido or N,N-dialkenylamido groups of the sizing agents of this invention are derived are: dihexylamine, dioctylamine (also called dicaprylamine) and, in particular, didodecylamine, dihexadecylamine and dioctadecenylamine (also called dilaurylamine, dipalmitylamine and dioleylamine respectively).

Because of its ready accessibility, dioctadecylamine (also called distearylamine) is particularly preferred. Commercially available technical mixtures of fatty amines of the indicated kind are particularly suitable. A preferred mixture of this kind is e.g. ARMEEN ®2 HT, which is a technical mixture of amines with an average molecular weight of 500 and which contains distearylamine as main component, together with other symmetrical and asymmetrical secondary amines as secondary components, said secondary components containing e.g. oleyl, lauryl and palmityl radicals.

Symmetrical and asymmetrical secondary amines of the above kind can be obtained from the corresponding previously mentioned fatty acids by methods which are known per se, by reacting the fatty acid with e.g. ammonia to give the intermediate nitrile, which is subsequently reacted by catalytic hydrogenation to give the secondary amine.

Specific representative of primary fatty amines from which the N-alkylmido or N-alkenylamido group of the sizing agents of this invention are derived are for example: octylamine (also called caprylamine), preferably dodecylamine, hexadecylamine or octadecenylamine (also called laurylamine, palmitylamine and oleylamine respectively) and, in particular, on account of its ready accessibility, octadecylamine (also called stearylamine). Specific representatives of fatty alcohols from which the alkyl or alkenyl ester groups of the sizing agents employed in this invention are derived are e.g. hexadecanol, oleyl alcohol and, on account of its ready accessibility, in particular octadecanol (also called stearyl alcohol).

Technical mixtures of the primary fatty amines or fatty alcohols of the indicated are also particularly suitable.

The sizing agents employed as component (A), which preferably contain a single carboxyl group in salt or acid form as anionic group and a single N,N-dialkylamido or N,N-dialkenylamido group, N-alkylamido or N-alkenylamido group or alkyl or alkenyl ester group of the indicated kind, are in general the anhydride of a N,N-$C_6$-$C_{22}$-dialkylamido- or N,N-$C_6$-$C_{22}$-dialkenylamidocarboxylic acid, the anhydride of a N-$C_6$-$C_{22}$alkylamido- or N,N-$C_6$-$C_{22}$alkenylamidocarboxylic acid, or the $C_6$-$C_{22}$alkyl or $C_6$-$C_{22}$alkenyl ester of an aromatic tetracarboxylic acid anhydride or salts thereof which are derived preferably from e.g. naphthalenetetracarboxylic acid, preferably benzophenonetetracarboxylic or pyromellitic acid as aromatic tetracarboxylic acid or, in particular, the anhydrides thereof, which are of especial interest owing to their ready accessibility. Accordingly, preferred sizing agents are compounds in the acid or free form e.g. of the formula

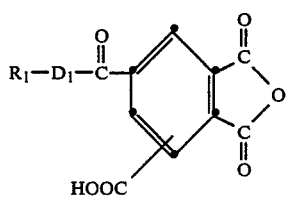

(1)

or

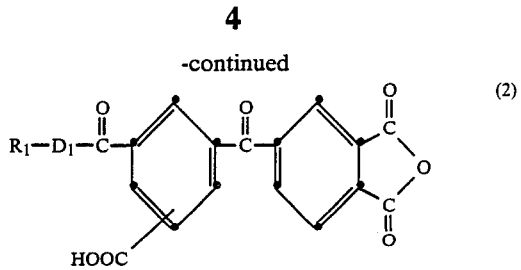

(2)

wherein $R_1$ is $C_6$-$C_{22}$alkyl or $C_6$-$C_{22}$alkenyl, $D_1$ is —O—, —NH— or —N($R_2$)—, and $R_2$ has the meaning of $R_1$, and $R_1$ and $R_2$ are different ore preferably identical radicals, with sizing agents which are compounds in the salt or acid form of the formula

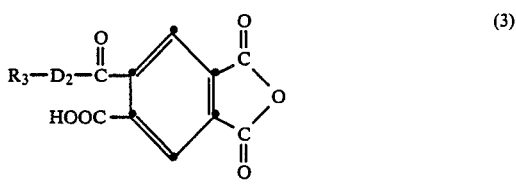

(3)

or

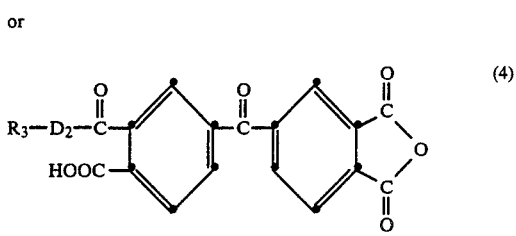

(4)

wherein $R_3$ is $C_{16}$-$C_{22}$alkyl or $C_{16}$-$C_{22}$alkenyl and $D_2$ is —O—, —H— or —N($R_3$)—, being particularly preferred.

Specific representatives of sizing agents of the formula (3) or (4) are e.g. compounds in the salt or acid form of the formulae

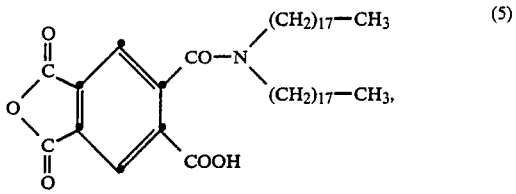

(5)

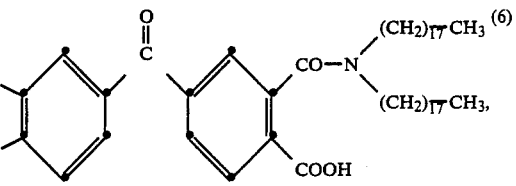

(6)

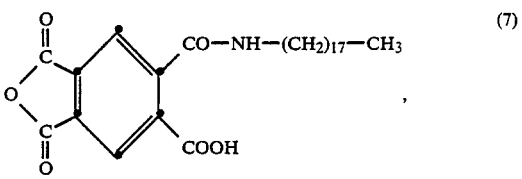

(7)

-continued

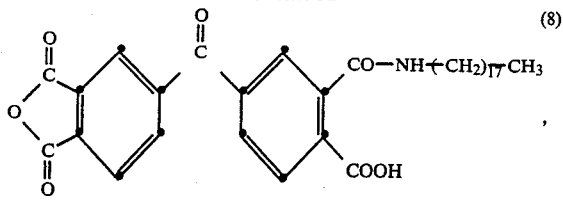  (8)

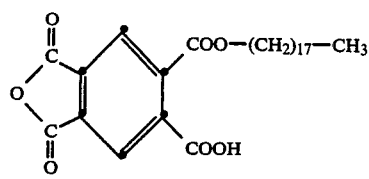  (9)

and

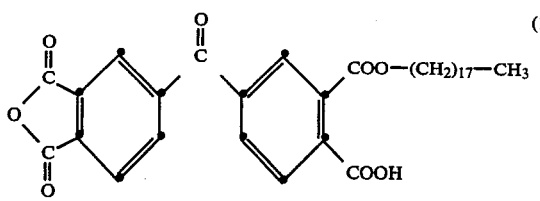  (10)

Before their use as component (A) in the paper-sizing process of this invention, the sizing agents do not need to be purified by recrystallisation after their synthesis, but can normally be used direct, i.e. without further working up.

Especially when adding the sizing agent (A) and the retention aid (B) separately (in any order) to the fibre suspension in the process of this invention for pulp-sizing paper or cardboard, it is convenient to add the sizing agent at least partly in salt form. As required, such salts can be prepared by converting the sizing agents (A), after their synthesis, wholly or partly into the corresponding salts by adding e.g. an alkylamine or alkanolamine containing a total of not more than 6 carbon atoms, e.g. trimethylamine, triethylamine, monoethanolamine or diethanolamine, preferably by adding ammonia or an alkali metal hydroxide, for example potassium hydroxide or, in particular, sodium hydroxide, normally in aqueous medium at room temperature (from about 15° to 25° C.). It is convenient to use an alkali metal hydroxide, e.g. potassium hydroxide or, preferably, sodium hydroxide, or especially ammonia, usually in the form of a dilute aqueous solution (about 1 to 10% by weight). It is advantageous to use generally not more than 3 moles, preferably from 0.1 to 1.5 moles and, most preferably, 0.9 to 1.1 moles of ammonia or alkali metal hydroxide per available acid group of the sizing agent. The sizing agents obtained in the form of their salts thus contain acid carboxyl, hydroxyl or sulfo groups which are at least partly converted into the —COO⊖M⊕, O⊖M⊕ or SO$_3$⊖M⊕ group, wherein M⊕ denotes the corresponding amine, ammonium or alkali metal cations.

Preferred sizing agents (A) of the indicated kind have molecular weights of about 300 to 1000, preferably from about 450 to 900. As already indicated, the sizing agents used as component (A) in the paper sizing process of this invention are novel compounds which can be prepared by methods which are known per se.

Accordingly, those compounds in the salt or acid form which are novel per se preferably have the formula

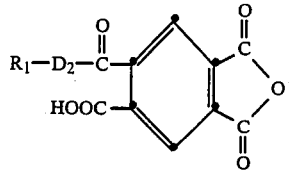  (11)

or

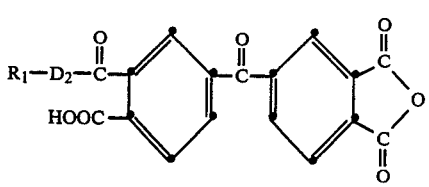  (12)

wherein $D_2$ is —O—, —NH— or —N($R_2$)—, and $R_1$ and $R_2$ are different or preferably identical radicals and are each independently of the other alkyl or alkenyl of 6 to 22, preferably 11 to 22 and, most preferably, 16 to 20 carbon atoms. The process for the preparation of these compounds comprises reacting an alcohol of the formula $R_1$—OH,   (13)

a primary amine of the formula $R_1$—NH$_2$   (14)

or a secondary amine of the formula

  (15)

wherein $R_1$ and $R_2$ each have the given meanings, with pyromellitic dianhydride or benzophenone-3,4,3',4'-tetracarboxylic dianhydride, in which reaction preferably 1 mole of fatty alcohol of formula (13), of primary fatty amine of formula (14) or of secondary fatty amine of formula (15) is used per mole of dianhydride of the indicated kind.

In the paper-sizing process of this invention, a polymeric cationic retention agent (B), which normally has a molecular weight of about at least 1000, preferably about 2000 to 2,000,000, is always used in addition to the novel anionic or acid sizing agent (A). Retention aids having a molecular weight in the range from 10,000 to 100,000 are particularly preferred. In principle, any commercially available retention aid is suitable for use in the process of this invention. Examples of conventional retention aids (B) which are particularly suitable for use, together with the sizing agent (A), in the process of this invention, are polyalkylenimines, adducts of epihalohydrin with reaction products of polyalkylenepolyamines and aliphatic dicarboxylic acids; adducts of epihalohydrin with reaction products of polyalkylenepolyamines, dicyandiamide and organic dicarboxylic acids which are free or esterified with alkanols; reaction products of dicyandiamide, formaldehyde, ammonium salts of strong inorganic acids and alkylenediamines or polyalkylenepolyamines; cationically modified starches or carbohydrates from carob beam gum or guar gum; copolymers based on polyamide amines and reaction products of epihalohydrins and polymerised diallyl amines.

Preferred adducts of epichlorohydrin with reaction products of polyalkylenepolyamines and aliphatic dicarboxylic acids are described e.g. in British Pat. No. 865,727; adducts of epichlorohydrin with reaction products of dicyandiamide and diethylenetriamine or triethylenetetramine are described e.g. in German "Offenlegungsschrift" 2,710,061 and in British Pat. No. 1,125,486; adducts of epichlorohydrin with reaction products of diethylenetriamine, dicyandiamide and dicarboxylic acids which are free or preferably esterified with lower alkanols, in particular dimethyl adipate, are described e.g. in British Pat. No. 1,125,486, and reaction products of dicyandimaide, formaldehyde, ammonium salts of strong inorganic acids and of ethylenediamine or triethylenetetraamine, are described e.g. in U.S. Pat. No. 3,491,064. Preferred cationically modified starches or carbohydrates from carob bean gum or guar gum are e.g. adducts of alkylene oxide with these starches or carbohydrates in which the alkylene oxide employed contains 2 or 3 carbon atoms in the alkylene moiety and quaternary ammonium groups. Copolymers based on polyamide amines have molecular weights of $10^3$ to $10^5$, preferably of $10^3$ to $10^4$, and are obtainable e.g. from aliphatic saturated dicarboxylic acids containing 2 to 10 carbon atoms, preferably 3 to 6 carbon atoms, preferably adipic acid, and polyalkylenepolyamines, e.g. polypropylenepolyamine and polyethylenepolyamine, preferably dimethylaminohydroxypropyl diethylenetriamine. They are described e.g. in the CTFA Cosmetic Ingredient Dictionary, 3rd edition 1982 (CFTA=Cosmetic Toiletry and Fragrance Association). Reaction products or epihalohydrins and polymerised diallyl amines preferably have molecular weights of 1000 to 2000 and are described e.g. in U.S. Pat. Nos. 3,700,623 and 4,729,794.

Typical examples of preferred retention aids (B) which are used together with the sizing agents (A) in the paper-sizing process of this invention are a maize or potato starch modified with a propylene oxide which contains quaternary ammonium groups, a 25% suspension of which in distilled water at 20° C. has a pH of 4.2 to 4.6, a polyethylenimine having a molecular weight of 10,000 to 100,000, an adduct of epichlorohydrin with a reaction product of triethylenetetraamine and dicyandiamide, an adduct of epichlorohydrin with a reaction product of diethylenetriamine, dicyandiamide and dimethyl adipate, a reaction product of diacyandiamide, formaldehyde, ammonium chloride and ethylenediamine, an adduct of epichlorohydrin with a poly-N-methyl diallyl amine, and a copolymer of adipic acid and dimethylaminohydroxypropyl diethylenetriamine.

In the process of this invention for the pulp-sizing of paper or cardboard, 0.02 to 3, preferably 0.05 to 3, in particular 0.1 to 0.8 percent by weight of the sizing agent (A), and 0.02 to 3, preferably 0.05 to 3, in particular 0.1 to 0.4 percent by weight of the retention aid (B) will normally be used, said amounts both being expressed as solids in (A) and (B) and based on the solids content of the fibre suspension. An amount of 0.02 to about 0.05 percent by weight of the sizing agent (A) and of the retention aid (B) suffices only for the size press control which is not ascertainable by means of conventional sizing tests (cf. for example the article "Control and Understanding of Size Press Pickup" by D. R. Dill in TAPPI Journal Vol. 57, No. 1, of January 1974, pp. 97–100) (TAPPI=Proceedings of the Technical Association of the Pulp and Paper Industry). The fibre suspension to which the sizing agent (A) and the retention aid (B) are added normally has a solids content of 0.1 to 5, preferably 0.3 to 3, most preferably 0.3 to 1 percent by weight, and a Schopper-Riegler freeness of about 10° to 60°, in particular 20° to 60°, preferably 20° to 45° and, most preferably, 25° to 35°. The suspension usually contains pulp, especially pulp obtained from coniferous wood, such as pinewood, or from hardwood, i.e. deciduous wood, such as beechwood, which pulp is prepared by conventional methods, e.g. by the sulfite process or, in particular, the sulfate process. In addition, the fibre suspension may contain groundwood. The fibre suspension may also contain alum-containing waste paper. Also suitable are pulp suspensions which are prepared by the CMP or CTMP process (chemimechanical and chemithermomechanial pulping processes, cf. for example the article "Developments in Refiner Mechanical Pulping" by S. A. Collicut and co-workers in TAPPI, Vol. 64, No. 6, of June 1981, pp. 57–61).

The fibre suspension can additionally contain organic or mineral fillers. Suitable organic fillers are e.g. synthetic pigments, for example polycondensates of urea or melamine and formaldehyde which have large specific surface areas, are in highly disperse form and are described e.g. in British Pat. Nos. 1,043,937 and 1,318,244, or mineral fillers such as montmorillonite, titanium dioxide, calcium sulfate and, in particular talcum, kaolin and/or chalk (calcium carbonate). The fibre suspension contains as a rule 0 to 40, preferably 5 to 25 and, most preferably, 15 to 20 percent by weight of the fillers of the indicated kind expressed as solids, based on the solids content of the fibre suspension.

The pH of the fibre suspensions can vary within a wide range, for example from about 3.5 to 10.

Upon addition of e.g. calcium carbonate, alkaline suspensions with a pH of e.g. over 7 to about 9, preferably from 7.5 to 8.5, are obtained. Acid fibre suspensions with a pH of 3.5 to 6.5, preferably from 5 to 6, can be obtained, in the absence of calcium cabonate, by adding acids, for example sulfuric acid or formic acid or, in particular, latent acid sulfates such as aluminium sulfate (alum).

Fibre suspensions which do not contain fillers may have a wide pH range from e.g. 3.5 to 10. Preferred fibre suspensions are those which have a pH in the range from about 6.5 to 9, preferably from 7 to 9, by adding chalk, and which are advantageous because possible corrosion in the sensitive paper machines is ruled out. In addition, the storage stability of paper or cardboard which has been sized in the pH range from 6.5 to 9 is markedly superior to that of paper or cardboard which has been sized in the pH range from 5 to 6.

The fibre suspensions may also contain additives, e.g. starch or its degradation products, which increase the fibre/fibre bond or fibre/filler bond.

It is also possible to add high molecular weight polymers of the acrylic series, e.g. polyacrylamides, with molecular weights of over 1,000,000 to the fibre suspensions as auxiliaries for retaining pulp fibre microparticles. Minimal amounts of about 0.005 to 0.02 percent by weight, expressed as solids in the polymer and based on the solids content of the fibre suspensions, suffice for this purpose.

The fibre suspension is further processed to paper or cardboard in the pulp sizing process of this invention, in a manner know per se, on sheet formers or, preferably, continuously in paper machines of conventional construction. After drying at about 100° to 140° C. for about ½ minute to 10 minutes, paper having a variable weight per unit area of e.g. 50 to 200 g/m² is obtained.

In the process of this invention for surface-sizing paper, the sizing liquor, which contains components (A) and (B), is applied to the paper e.g. by spraying, preferably by padding, usually at room temperature (15°-25° C.). The impregnated paper is then dried at 60° to 140° C., preferably from 90° to 110° C., for 0.1 to 10 minutes, preferably from 2 to 6 minutes. After it has ben dried, the paper has a surface coating of sizing agent and retention aid of 5 to 150 mg/m², preferably of 60 to 120 mg/m².

The paper to be sized can be paper of any kind having any weight per unit area, for example paper or cardboard made of bleached or unbleached sulfite or sulfate cellulose.

As mentioned at the outset, the aqueous composition for carrying out the paper-sizing process of this invention contains the sizing agent (A), in addition to optional customary auxiliaries, provided the sizing agent and the retention aid (B) are added separately to the fibre suspension for pulp sizing. In this case the composition contains the sizing agent entirely, or preferably partly, in salt form (obtained by concurrently using e.g. ammonia, an alkylamine or alkanolamine or an alkali metal hydroxide of the indicated kind in the ratios stated above). In general, such compositions contain 5 to 30 percent by weight, preferably 5 to 20 percent by weight, of the sizing agent which is at least partly in salt form, expressed as solids and based on the weight of the aqueous composition.

On the other hand, if the sizing agent (A) and the retention aid (B) are added simultaneously to the fibre suspension for pulp-sizing the aqueous composition contains, in addition to the optional customary auxiliaries, (A) 2 to 40 percent by weight, preferably 5 to 30 percent by weight, and, most preferably, 5 to 10 percent by weight of sizing agent (calculated as solid), based on the total weight of the aqueous composition, which sizing agent is optionally in salt form, and (B) 0.1 to 20 percent by weight, preferably 0.5 to 10 percent by weight, most preferably 3 to 8 percent by weight of retention aid (calculated as solid), based on the total weight of the aqueous composition.

The aqueous compositions of the indicated kind may contain surface-active compounds as customary auxiliaries, e.g. dispersants or also emulsifiers and/or water-soluble organic solvents. Examples of suitable dispersants and emulsifiers are conventional ligninsulfonates, lignincarboxylates, carboxymethyl cellulose, adducts of ethylene oxide and alkyl phenols, fatty amines, fatty alcohols or fatty acids, fatty acid esters of polyhydric alcohols, substituted benzimidazoles, or condensates of formaldehyde and aromatic sulfonic acids, preferably naphthalenesulfonic acids. Further surface-active compounds are preferably anionic surfactants, in particular sulfate surfactants, e.g. diethanolamine lauryl sulfate, sodium lauryl sulfate or ethoxylated lauryl sulfates. Possible water-soluble organic solvents are aliphatic ethers of 1 to 10 carbon atoms, e.g. dioxane, ethylene glycol n-butyl ether or diethylene glycol monobutyl ether, or alcohols of 1 to 4 carbon atoms, e.g. isopropanol, ethanol or methanol.

If the aqueous compositions contain auxiliaries of the indicated kind, the ratio of component (A) to auxiliaries in the compositions is 1:0.02 to 1:0.3, preferably 1:0.05 to 1:0.1, based on the solids content of the sizing agent and the auxiliaries.

The compositions are formulated in conventional manner by stirring the sizing agent (A) together with retention acid (B), or the sizing agent (A), usually partly in salt form, by itself either in the melt state or preferably in the solid state, in particular in power form, normally in the presence of glass beads and, if necessary, of an emulsifier (if the sizing agent is in the melt state) or a dispersant (if the sizing agent is in powder form), at a maximum temperature of 90° C., preferably of about 50° to 85° C. if emulsions are prepared, and preferably at about 15° to 25° C. if dispersions are prepared, to give storage stable, homogeneous emulsions or, preferably, dispersions which can be further diluted. As the sizing agents together with the retention aids, or the sizing agents which are entirely or at least partly in salt form, are usually self-dispersing or self-emulsifying, the use of dispersants or emulsifiers is in general not absolutely necessary. This also applies to the optional use of solvents and/or surfactants, which are employed only if the storage stability of the dispersions or emulsions is insufficient.

For surface-sizing paper, the requisite sizing liquor is prepared by diluting the emulsions or dispersions referred to above with water, which emulsions or dispersions contain the sizing agent (A) as well as the retention aid (B). The emulsions or dispersions are diluted such that the sizing liquor obtained contains (A) 0.02 to 0.4, preferably 0.05 to 3 and, most preferably, 0.05 to 1 percent by weight of sizing agent (calculated as solid), based on the total weight of said sizing liquor, said sizing agent being optionally in salt form, and (B) 0.01 to 0.2, preferably 0.05 to 0.1 and, most preferably, 0.3 to 0.8 percent by weight of retention aid (calculated as solid), based on the total weight of the aqueous sizing liquor.

An advantage of the process of this invention is that, for pulp-sizing, fibre suspensions of widely differing kind can be processed with relatively small amounts of sizing agent and retention aid, in simple manner, to give paper which has good sizing properties (alkali drop test, ink flotation time and, in particular, water absorption according to Cobb). This applies also to surface sizing, in which the good sizing effects are obtained with small amounts of sizing agent and retention aid. In particular, the small amounts permit a rapid mode of operation, so that good surface-sizing effects are obtained in the drying temperature range from e.g. 90° to 110° C. over about 20 to 40 seconds. The paper which is pulp-sized by the process of this invention has good mechanical properties, i.e. good strength, especially good tear strength. A good reproducibility of the process is ensured in pulp-sizing as well as surface-sizing. In particular, it is possible in pulp-sizing to process fibre suspensions which contain groundwood or waste paper. The compatibility of the sizing agent employed in the process of the invention with different fillers, e.g. kaolin, and also with other ingredients, e.g. alum, in an acid range of the fibre suspensions for pulp-sizing, is also advantageous.

The sizing agents and retention aids employed in the process of this invention are readily compatible with the auxiliaries conventionally used in the paper manufacturing industry, for example dyes, pigments, binders, and especially fluorescent whitening agents and other auxiliaries. As mentioned at the outset, the sizing agents and retention aids employed in the process of this invention are readily accessible and inexpensive. Further, the sizing agents and retention aids do not have an undesirable propensity to foam. In addition, the degree of whiteness of the sized paper is not materially affected by the sizing and may even be improved both in pulp-sizing and in surface-sizing. In particular, the surprisingly good storage stability of the sizing agent dispersions of the indicated kind is most advantageous.

In the following working Examples, parts and percentages are by weight.

PREPARATION OF NOVEL COMPOUNDS AS SIZING AGENTS

EXAMPLE 1

21.8 parts (0.1 mole) of pyromellitic dianhydride, 50.0 parts (0.1 mole) of a technical mixture of distearylamines (ARMEEN®2 HT) with an average molecular weight of 500, and 200 parts of toluene are heated to c. 111° C. and stirred for 8 hours at this temperature, when gradually a clear solution forms. The solvent is then removed by vacuum distillation, affording 67.5 parts of the compound corresponding essentially to the formula (5) as a yellowish viscous substance.

EXAMPLE 2

The procedure of Example 1 is repeated, using 32.2 parts (0.1 mole) of benzophenonetetracarboxylic dianhydride (instead of 21.8 parts of pyromellitic dianhydride), to give 78 parts of a compound corresponding essentially to formula (6) as a viscous substance.

EXAMPLE 3

A solution of 26.8 parts (0.1 mole) of octadecylamine in 150 parts of chloroform is added at 20° C. over 15 minutes to a suspension of 21.8 parts (0.1 mole) of pyromellitic dianhydride in 200 parts of chloroform, whereupon the temperature of the reaction mixture rises to 37° C. The reaction mixture is further heated to reflux temperature of c. 62° C. and stirred at this temperature for 5 hours to form a clear solution. The solvent is subsequently removed by vacuum distillation, affording 46.5 parts of the compound of formula (7) as a white powder with a melting point of 143°-149° C.

EXAMPLE 4

The procedure of Example 3 is repeated, using 32.2 parts (0.1 mole) of benzophenonetetracarboxylic dianhydride (instead of 21.8 parts of pyromellitic dianhydride), to give 29 parts of a compound corresponding to formula (8) as a white powder with a melting point of 145°-151° C.

EXAMPLE 5

10.9 parts (0.05 mole) of pyromellitic dianhydride are dissolved in 150 parts of dioxane and the solution is heated to reflux temperature of c. 102° C. Then a solution of 13.5 parts (0.05 mole) of stearyl alcohol in 50 parts of dioxane is added to the above solution at c. 102° C. over 2 hours and the reaction mixture is stirred for 20 hours at reflux temperature of c. 102° C. The solvent is then removed by vacuum distillation, affording 23.0 parts of the compound of formula (7) as a white powder with a melting point of 135°-138° C.

EXAMPLE 6

The procedure of Example 5 is repeated, using 16.1 parts (0.05 mole) of benzophenonetetracarboxylic dianhydride (instead of 10.9 parts of pyromellitic dianhydride), to give 29.5 parts of the compound of formula (10) as a yellowish viscous substance.

APPLICATION EXAMPLES

EXAMPLES 7 TO 10

To a fibre suspension which contains bleached birch sulfate pulp and pine sulfate pulp in a weight ratio of 1:1 in water of 10° (German water hardness), and which has a Schopper-Riegler Freeness of 35° and a solids content of 0.5%, are added 20% of chalk as filler and then 0.01% of PERCOL®292 (cationic high molecular weight (MG $<1.10^7$) polyacrylamide) as auxiliary for retaining pulp fibre microparticles. The pH of the fibre suspension is as indicated in Table I below. The percentages refer to solids in filler and assistant, based on the solids content of the fiber suspension.

Formulations of the sizing agent are prepared by stirring 7% of each of the indicated sizing agents in powder form (obtained as crude product) with 3.5% of POLYMIN®P (polyethylenimine with a molecular weight of 10.000 to 100.000) as retention aid, in the presence of deionised water and of glass beads having a diameter 2 mm, at room temperature (15° to 25° C.). The dispersions so obtained are pourable, homogeneous and storage stable. The percentages refer to solids in fillers and retention aids, based on the total weight of the formulation.

The aqueous formulation of the sizng agent and the retention aid is then added to the fibre suspension in such a manner as to give the solids content of sizing agent, based on the solids content of the fibre suspension, indicated in Table I. The fibre suspension is then processed in a laboratory "Formette Dynamique" sheet former (supplied by Allimand, Grenoble, France) to paper sheets which, after they have been dried at 130° C. for 3 minutes, have a weight per unit area of 80 g/m².

Both surfaces of the paper sheets so obtained, i.e. the surface obtained on the wire side of the sheet former and the adjacent or top side, are tested for their sizing properties. This is done by measuring the water absorption according to Cobb over 30 seconds (WA Cobb$_{30}$) in accordance with DIN 53 132. The results of the WA Cobb$_{30}$ measurements in g/m² of the wire side (WS) and top side (TS) after drying at 130° C. and storage for 1 day at 23° C. and 50% relative humidity are reported in Table I. The lower the water absorption, the better the paper sizing. WA Cobb$_{30}$ values above 100 denote a completely unsatisfactory sizing of the paper.

TABLE I

| Example | Sizing agent | Amounts of sizing agent (%) | pH of the fibre suspension | WA Cobb$_{30}$ (g/m²) after drying | | after storage for 1 day | |
|---|---|---|---|---|---|---|---|
| | | | | WS | TS | WS | TS |
| 7 | compound of Example 1 | 1 | 8.3 | 28 | 17 | 20 | 14 |
| 8 | compound of | 2 | 8.1 | 13 | 18 | 11 | 13 |

TABLE I-continued

| Example | Sizing agent | Amounts of sizing agent (%) | pH of the fibre suspension | WA Cobb$_{30}$ (g/m$^2$) | | | |
|---|---|---|---|---|---|---|---|
| | | | | after drying | | after storage for 1 day | |
| | | | | WS | TS | WS | TS |
| 9 | Example 2 compound of Example 3 | 2 | 8.5 | 33 | 17 | — | — |
| 10 | compound of Example 4 | 2 | 8.1 | 32 | 18 | 31 | 14 |

Similar results are otained by replacing POLY-MIN®P as cationic retention aid with CATO®110 (cationically modified starch which is modified with a propylene oxide containing ammonium groups; pH of a 25% suspension in distilled water at 20° C.=4.2 to 4.6), POSAMYL®E7 (cationically modified starch with a nitrogen content of 0.4%), a native potato starch cationically modified with trimethylglycidylammonium chloride and having a nitrogen content of 1.3%, a condensate of dicyandiamide and triethylenetramine which is further reacted with epichlorohydrin and is prepared in accordance with e.g. Example 2 of German "Offenlegungsschrift" 2,710,061, an adduct of epichlorohydrin and a reaction product of diethylenediamine and adipic acid, prepared in accordance with e.g. Example 1 of British Pat. No. 865,727, a reaction product of dicyandiamide, formaldehyde, ammonium chloride and ethylenediamine, prepared in accordance with e.g. Example 1 of U.S. Pat. No. 3,491,064, or RETAMINOL®K (polyethylenimine of mol wt 20,000 to 40,000). Mixtures of the retention aids of the above indicated kind are also suitable. To obtain good results, it can be advantageous to add dispersants, in particular condensates of formaldehyde and naphthalenesulfonic acids, or carboxymethyl cellulose. However, only a poor sizing with Cobb values of about 150 to 200 are obtained by using a sizing agent of any one of Examples 1 to 4, but without retention aid, or a retention aid of the above indicated kind but without a sizing agent.

EXAMPLES 11 TO 16

The procedures of Examples 7 to 10 are repeated, except that the sizing agent and retention aid are added separately of the fibre suspension, by stirring 7, 10 or 15% of sizing agent in powder form, at room temperature (15°-25° C.), in the presence of water and glass beads, with an aqueous 5% ammonia solution to give a self-emulsifying, pourable and storage stable emulsion of the sizing agent formulations as indicated in Table II. The val % indicates the number of equivalents of ammonia for 100 equivalents, based on the number of acid groups contained in the respective sizing agent. The indicated amount of the retention aid POLYMIN®P, expressed as solids, is added to the fibre suspension 10 seconds after the addition of the indicated amount of sizing agent, expressed as solids, said amounts being based on the solids content of the fibre suspension. The sizing results are also reported in Table II.

TABLE II

| Example | Formulation of the sizing agent | Amount of the sizing agent (%) | Amount of retention-aid (%) | pH of the fibre suspension | WA Cobb$_{30}$ (g/m$^2$) after drying | |
|---|---|---|---|---|---|---|
| | | | | | WS | TS |
| 11 | 15% of the compound of Example 1 100 val % of ammonia | 0.50 | 0.25 | 8.6 | 19 | 14 |
| 12 | 15% of the compound of Example 2 295 val % of ammonia | 0.50 | 0.25 | 8.7 | 20 | 16 |
| 13 | 10% of the compound of Example 3 100 val % of ammonia | 1.0 | 0.75 | 8.5 | 60 | 19 |
| 14 | 10% of the compound of Example 4 100 val % of ammonia | 0.50 | 0.25 | 8.4 | 23 | 14 |
| 15 | 10% of the compound of Example 5 100 val % of ammonia | 1.0 | 0.75 | 8.6 | 25 | 20 |
| 16 | 10% of the compound of Example 6 100 val % of ammonia | 1.0 | 0.75 | 8.5 | 27 | 17 |

Sizing results analogous to those reported in Table II are obtained by using from 10 to 200 val % of ammonia or sodium hydroxide (as 5% aqueous solutions) for formulating the sizing agent.

Similar results are also obtained by first adding the retention aid to the fibre suspension and subsequently adding the sizing agent 10 seconds later. The same also applies by dispensing with the addition of PERCOL®292 and/or of a filler. Similar results are likewise obtained by using talcum or kaolin as filler instead of chalk or by additionally using alum. Good sizing results are also obtained by using fibre suspensions which contain groundwood.

What is claimed is:

1. A process for sizing paper or cardboard, which comprises adding to an aqueous cellulose containing fiber suspension or to the surface of a cellulose fiber containing paper or cardboard
   (A) one aromatic sizing agent selected from a compound in the acid or salt form of the formula

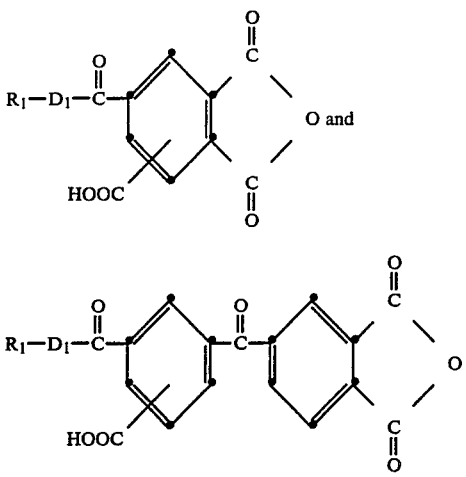

wherein $D_1$ is —NH— or —N($R_2$)—, and each of $R_1$ and $R_2$ is independently $C_6$–$C_{22}$alkyl or $C_6$–$C_{22}$alkenyl, provided that $R_1$ is $C_6$–$C_{22}$alkenyl where $D_1$ is —NH—, and (B) one polymeric cationic retention aid.

2. A process of claim 1 for pulp-sizing paper or cardboard, which comprises adding components (A) and (B), in any order or simultaneously, to an aqueous cellulose-containing fiber suspension which may or may not contain fillers.

3. A process of claim 1 for surface-sizing paper, which comprises impregnating said paper with an aqueous sizing liquor that contains components (A) and (B) and drying the impregnated paper.

4. A process of claim 1, wherein the retention aid (B) has a molecular weight in the range from 1000 to 2,000,000.

5. A process of claim 1, wherein the retention aid (B) is selected from the group consisting of a polyalkylenimine, an adduct of epihalohydrin with a reaction product of a polyalkylenepolyamine and an aliphatic dicarboxylic acid; an adduct of epihalohydrin with a reaction product of a polyalkylenepolyamine, dicyandiamide and an organic dicarboxylic acid which is free or esterified with an alkanol; a reaction product of dicyandiamide, formaldehyde, an ammonium salt of a strong inorganic acid and an alkylenediamine or a polyalkylenepolyamine; a cationically modified starch or carbohydrate from carob bean gum or guar gum; a copolymer based on a polyamide amine or a reaction product of an epihalohydrin and a polymerised diallyl amine.

6. A process of claim 1 for pulp-sizing paper or cardboard, which comprises using 0.02 to 3 percent by weight of the sizing agent (A) and 0.02 to 3 percent by weight of the retention aid (B), both amounts being expressed as solids in (A) and (B) and based on the solids content of the fiber suspension.

7. A process of claim 1 for pulp-sizing paper or cardboard, which comprises adding a filler, selected from the group consisting of a condensate of formaldehyde and urea, titanium dioxide, talcum, kaolin, montmorillonite or chalk.

8. A process of claim 1 for pulp-sizing paper or cardboard, which comprises adding a filler selected from the group consisting of talcum, kaolin or chalk as filler.

9. A process of claim 1 for pulp-sizing paper or cardboard, wherein the fiber suspension has a pH value of 3.5 to 10.

10. A process of claim 1 for pulp-sizing paper or cardboard, wherein the fiber suspension has a pH value of 6.5 to 9.

11. A process of claim 1 for pulp-sizing paper or cardboard, wherein the fiber suspension has a Schopper-Riegler freeness of 10° to 60° and a solids content of 0.1 to 5 percent by weight.

12. A process of claim 1 for pulp-sizing paper or cardboard, wherein the fiber suspension contains pulp selected from the group consisting, groundwood, alum-containing waste paper or mixtures thereof.

13. A process of claim 1 for surface-sizing paper, wherein the paper is dried in the temperature range from 60° to 140° C.

14. A process of claim 1 for surface-sizing paper, wherein the paper is dried in the temperature range from 90° to 110° C.

15. A process of claim 1, wherein component (A) is a sizing agent which is compound in the acid or salt form of the formula

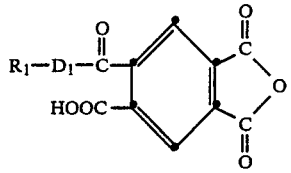

or

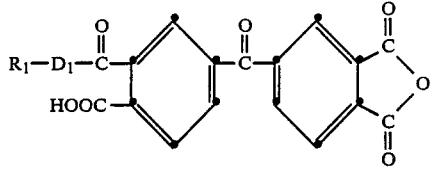

wherein $R_1$ and $R_2$ are the same and are $C_{16}$–$C_{22}$alkyl or $C_{16}$–$C_{22}$alkenyl.

* * * * *